(12) United States Patent
Aftab et al.

(10) Patent No.: US 11,116,759 B2
(45) Date of Patent: Sep. 14, 2021

(54) METHOD OF TREATING CANCER

(71) Applicant: Exelixis, Inc., Alameda, CA (US)

(72) Inventors: Dana T. Aftab, San Rafael, CA (US); Frauke Schimmoller, Menlo Park, CA (US)

(73) Assignee: Exelixis, Inc., Alameda, CA (US)

( * ) Notice: Subject to any disclaimer, the term of this patent is extended or adjusted under 35 U.S.C. 154(b) by 0 days.

(21) Appl. No.: 16/142,691

(22) Filed: Sep. 26, 2018

(65) Prior Publication Data

US 2019/0091215 A1     Mar. 28, 2019

Related U.S. Application Data

(63) Continuation of application No. 14/933,801, filed on Nov. 5, 2015, now abandoned, which is a continuation of application No. 14/668,312, filed on Mar. 25, 2015, now abandoned, which is a continuation of application No. 13/438,964, filed on Apr. 4, 2012, now abandoned.

(60) Provisional application No. 61/471,367, filed on Apr. 4, 2011.

(51) Int. Cl.
*A61K 31/47*    (2006.01)
*A61P 35/04*    (2006.01)

(52) U.S. Cl.
CPC .............. *A61K 31/47* (2013.01); *A61P 35/04* (2018.01)

(58) Field of Classification Search
CPC ................................. A61K 31/47; A61P 35/04
See application file for complete search history.

(56) References Cited

U.S. PATENT DOCUMENTS

| | | |
|---|---|---|
| 7,579,473 B2 | 8/2009 | Bannen et al. |
| 7,977,345 B2 | 7/2011 | Bannen et al. |
| 7,999,006 B2 | 8/2011 | Lamb |
| 8,067,436 B2 | 11/2011 | Bannen |
| 8,178,532 B2 | 5/2012 | Bannen et al. |
| 8,314,232 B2 | 11/2012 | Deschamps et al. |
| 8,476,298 B2 | 7/2013 | Bannen et al. |
| 8,497,284 B2 | 7/2013 | Bannen et al. |
| 8,673,912 B2 | 3/2014 | Cannon et al. |
| 8,877,776 B2 | 11/2014 | Brown et al. |
| 9,174,947 B2 | 11/2015 | Bannen et al. |
| 9,365,516 B2 | 6/2016 | Wilson et al. |
| 9,717,720 B2 | 8/2017 | Wilson et al. |
| 9,724,342 B2 | 8/2017 | Wilson et al. |
| 9,809,549 B2 | 11/2017 | Brown et al. |
| 9,861,624 B2 | 1/2018 | Aftab et al. |
| 2007/0054928 A1* | 3/2007 | Bannen ............... A61P 19/00 514/266.2 |
| 2007/0244116 A1 | 10/2007 | Bannen et al. |
| 2008/0161305 A1 | 7/2008 | Forsyth et al. |
| 2009/0274693 A1 | 11/2009 | Gilmer et al. |
| 2011/0077233 A1 | 3/2011 | Bannen et al. |
| 2012/0070368 A1 | 3/2012 | Bannen et al. |
| 2012/0184523 A1 | 7/2012 | Bannen et al. |
| 2012/0252840 A1 | 10/2012 | Aftab et al. |
| 2012/0282179 A1 | 11/2012 | Aftab et al. |
| 2013/0030172 A1 | 1/2013 | Wilson et al. |
| 2013/0142790 A1 | 6/2013 | Gilmer et al. |
| 2013/0143881 A1 | 6/2013 | Cannon et al. |
| 2013/0150363 A1 | 6/2013 | Gilmer et al. |
| 2013/0197230 A1 | 8/2013 | Wilson et al. |
| 2013/0252940 A1 | 9/2013 | Bannen et al. |
| 2013/0252956 A1 | 9/2013 | Wilson et al. |
| 2013/0330377 A1 | 12/2013 | Wilson et al. |
| 2013/0337015 A1 | 12/2013 | Wilson et al. |
| 2014/0057908 A1 | 2/2014 | Smith et al. |
| 2014/0057943 A1 | 2/2014 | Smith et al. |
| 2014/0066444 A1 | 3/2014 | Smith et al. |
| 2014/0155396 A1 | 6/2014 | Bannen et al. |
| 2014/0179736 A1 | 6/2014 | Schwab et al. |
| 2014/0200242 A1 | 7/2014 | Wilson et al. |
| 2014/0228401 A1 | 8/2014 | Aftab et al. |
| 2014/0256938 A1 | 9/2014 | Wilson et al. |
| 2014/0302012 A1 | 10/2014 | Aftab et al. |
| 2014/0323522 A1 | 10/2014 | Aftab et al. |
| 2015/0057310 A1 | 2/2015 | Brown et al. |
| 2015/0196545 A1 | 7/2015 | Aftab et al. |
| 2015/0202196 A1 | 7/2015 | Bannen et al. |
| 2015/0376133 A1 | 12/2015 | Bannen et al. |
| 2016/0000772 A1 | 1/2016 | Aftab et al. |
| 2016/0022662 A1 | 1/2016 | Decillis et al. |
| 2016/0051532 A1 | 2/2016 | Aftab et al. |
| 2016/0185725 A1 | 6/2016 | Bannen et al. |
| 2016/0220554 A1 | 8/2016 | Smith et al. |
| 2016/0229805 A1 | 8/2016 | Wilson et al. |
| 2017/0057921 A1 | 3/2017 | Wilson et al. |
| 2017/0143689 A1 | 5/2017 | Wilson et al. |
| 2017/0266178 A1 | 9/2017 | Wilson et al. |
| 2017/0275251 A1 | 9/2017 | Brown et al. |
| 2018/0002289 A1 | 1/2018 | Brown et al. |
| 2018/0037552 A1 | 2/2018 | Brown et al. |
| 2019/0091215 A1 | 3/2019 | Aftab et al. |

OTHER PUBLICATIONS

Sato et al., "The biology and management of uveal melanoma," Curr. Oncol. Rep. Sep. 2008;10(5):431-38. PMID: 18706273. (Year: 2008).*

(Continued)

*Primary Examiner* — Theodore R. Howell
(74) *Attorney, Agent, or Firm* — Honigman LLP; Heidi M. Berven

(57) ABSTRACT

This invention is directed to the treatment of cancer, particularly ocular melanoma, with a dual inhibitor of MET and VEGF such as Compound 1.

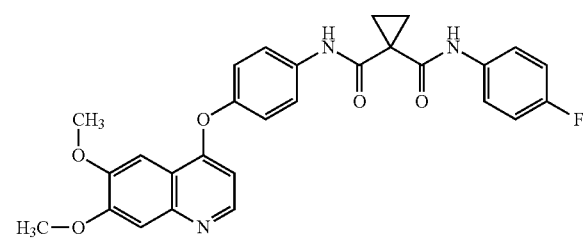

4 Claims, 5 Drawing Sheets

(56) References Cited

OTHER PUBLICATIONS

Berge et al., "Pharmaceutical salts," J. Pharm. Sci. Jan. 1997;66(1):1-19. PMID: 833720. (Year: 1977).*
Daud, et al., "Activity of cabozaritinib in metastatic uveal melanoma: Updated results from a phase II randomized discontinuation trial (RDT)", J Clin Oncol 31, 2013 (suppl; abstr 9094), Jun. 1, 2013.
National Cancer Institute (http://www.cancer.gov/drugdictionary?cdrid=461103) (accessed Aug. 8, 2013).
Nechushtan et al., 22nd EORTC-NCI-AACR Symposium art molecular targets and cancer therapeutics, Nov. 16-19, 2010, Berlin, Germany.
Yakes, et al., "Cabozantinib (XL184), a Novel MET and VEGFR2 Inhibitor, Simultaneously Suppresses Metastasis, Angiogenesis, and Tumor Growth.", Molecular Cancer Therapeutics, 10(12):2298-2308, 2011.
Yan, et al., "MicroRNA-34a inhibits Uveal Melanoma Cell Proliferation and Migration through Downregulation of c-Met", Investigative Opthamology & Visual Science, vol. 50, No. 4, pp. 1559-1665, Apr. 2009.
Abdel-Rahman, et al., "MET Oncogene Inhibition as a Potential Target of Therapy for Uveal Melanomas", Investigative Opthamology & Visual Science, vol. 51, No. 7, Jul. 2010.
McLaughlin, et al., "Incidence of Noncutaneous Melanomas in the U.S.", Cancer, vol. 103, No. 5, pp. 1000-1007, Mar. 1, 2005.
Berge et al., "Pharmaceutical salts," J Pharm. Sci., 66 (1): 1-19 (Jan. 1977).

* cited by examiner

| Table 2. Baseline Mutation Status (N = 50) | | | | | |
|---|---|---|---|---|---|
|  | BRAF (V600E) | NRAS | KIT | GNAQ | GNA11 |
| Mutation detected, n | 15 (10) | 7 | 0 | 5 | 4 |
| Mutation not detected, n | 33 | 29 | 34 | 6 | 3 |
| Not tested, n | 2 | 14 | 16 | 39 | 43 |

Mutation data based on in-house analyses of archival tumor tissue at Exelixis and investigator reporting. Analyses for ocular melanoma were limited to commonly mutated GNAQ and GNA11 (when available), as well as BRAF. Analyses for non-ocular subtypes were generally limited to BRAF, NRAS, and KIT.

FIG. 2

| Table 3. Summary of Response (N = 58)[a] | |
|---|---|
| Best ORR, n (%) | |
| Confirmed PR | 2 (3) |
| Stable disease (SD)[b] | 37 (64) |
| – Unconfirmed PR | 1 (2) |
| Progressive disease | 12 (21) |
| Week 12 DCR[c], n (%) | 26 (45) |
| DCR by LDH status, n (%) | |
| Normal LDH | 20 (34) |
| Elevated LDH (> ULN) | 6 (10) |
| DCR by subtype, n (%) | |
| Cutaneous | 15 (26) |
| Mucosal | 3 (5) |
| Ocular | 8 (14) |

PR, partial response
[a] No post-baseline tumor assessments available for 7 patients
[b] Unconfirmed PR included
[c] Disease control rate (DCR) defined as PR + SD at Week 12

FIG. 3

Table 5. Overview of Patients with Best Response of SD or PR (N=31)

| Patient | Subtype | Sex (M/F) | Visceral Metastasis | LDH Elevated at Baseline | Weeks on Study Treatment | Best Response on Study Treatment | No. of Prior Treatments | Most Recent Prior Treatment | Best Response on Prior Treatment | Mutation Status[a] |
|---|---|---|---|---|---|---|---|---|---|---|
| 1 | Cutaneous | F | | | 20 | PR | 1 | doxorubicin | NA | BRAF(V600E) |
| 2 | Cutaneous | M | ✓ | | 14+ | PR | 2 | dacarbazine | NA | UNK |
| 3 | Cutaneous | M | ✓ | | 14 | PR | 0 | - | - | ND |
| 4 | Cutaneous | M | ✓ | | 49 | SD | 1 | peginterferon alfa-2B/ temozolomide | SD | BRAF(V600E) |
| 5 | Ocular | F | ✓ | | 48+ | SD | UNK | - | - | UNK |
| 6 | Ocular | F | | | 46 | SD | 1 | temozolomide | NA | GNAQ |
| 7 | Cutaneous | F | ✓ | ✓ | 44+ | SD | 0 | - | - | BRAF(V600E) |
| 8 | Cutaneous | F | | | 42 | SD | 0 | - | - | ND |
| 9 | Cutaneous | M | | | 40+ | SD | 2 | imatinib | NA | ND |
| 10 | Cutaneous | F | ✓ | | 39 | SD | 1 | docetaxel/investigational | SD | UNK |
| 11 | Cutaneous | M | ✓ | | 36 | SD | 1 | temozolomide | NA | ND |
| 12 | Cutaneous | M | | | 31 | SD | 1 | IL-2/temozolomide/sorafenib | SD | UNK |
| 13 | Mucosal | F | ✓ | ✓ | 28+ | SD | 2 | carboplatin/paclitaxel | NA | ND |
| 14 | Ocular | M | ✓ | | 28+ | SD | 0 | - | - | UNK |
| 15 | Ocular | F | ✓ | | 27+ | SD | 1 | fotemustine | NA | GNA11 |
| 16 | Mucosal | F | ✓ | | 26+ | SD | 3 | paclitaxel | SD | BRAF,NRAS |
| 17 | Cutaneous | M | ✓ | | 25+ | SD | 2 | temozolomide | NA | BRAF(V600E) |
| 18 | Ocular | M | | ✓ | 22 | SD | 2 | sorafenib | NA | UNK |
| 19 | Cutaneous | F | | | 22 | SD | 1 | temozolomide | SD | NRAS |
| 20 | Ocular | F | ✓ | ✓ | 20 | SD | 2 | dacarbazine | PR | UNK |

FIG. 4A

Table 5. Overview of Patients with Best Response of SD or PR (N=31)

| Patient | Subtype | Sex (M/F) | Visceral Metastasis | LDH Elevated at Baseline | Weeks on Study Treatment | Best Response on Study Treatment | No. of Prior Treatments | Most Recent Prior Treatment | Best Response on Prior Treatment | Mutation Status[a] |
|---|---|---|---|---|---|---|---|---|---|---|
| 21 | Cutaneous | M | ✓ | | 19 | SD | UNK | - | - | ND |
| 22 | Ocular | F | ✓ | ✓ | 19 | SD | 4 | investigational | NA | GNA11 |
| 23 | Cutaneous | M | ✓ | | 19 | SD | 2 | dasatinib | SD | UNK |
| 24 | Mucosal | F | | ✓ | 16+ | SD | 1 | vinblastine | NA | ND |
| 25 | Cutaneous | M | | | 16 | SD | 1 | cisplatin/temozolomide/ vinblastine | NA | BRAF |
| 26 | Ocular | M | ✓ | | 15+ | SD | 0 | - | - | UNK |
| 27 | Mucosal | M | | | 11 | SD | 0 | - | - | BRAF(V600E) |
| 28 | Ocular | M | ✓ | ✓ | 9 | SD | 1 | cisplatin/dacarbazine | SD | GNA11 |
| 29 | Ocular | F | ✓ | ✓ | 7 | SD | 2 | carboplatin/paclitaxel | NA | UNK |
| 30 | Cutaneous | M | ✓ | ✓ | 7 | SD | 2 | temozolomide | NA | ND |
| 31 | Cutaneous | M | ✓ | ✓ | 6 | SD | 2 | IL-2 (high dose) | NA | UNK |

IL-2, interleukin-2; NA, not available; ND, no mutation detected in sequenced genes; PR, partial response; SD, stable disease; UNK, unknown

[a]Mutation data based on in-house analyses of archival tumor tissue at Exelixis and investigator reporting. Analyses for ocular melanomas were primarily focused on commonly mutated GNAQ and GNA11. Analyses for nonocular subtypes typically included BRAF, NRAS, and KIT.

FIG. 4B

METHOD OF TREATING CANCER

CROSS-REFERENCE TO RELATED APPLICATIONS

This application is a continuation application of U.S. Ser. No. 14/933,801, filed Nov. 5, 2015, which is a continuation application of U.S. Ser. No. 14/668,312, filed Mar. 25, 2015, which is a continuation application of U.S. Ser. No. 13/438,964, filed Apr. 4, 2012, which claims the benefit of U.S. provisional patent application Ser. No. 61/471,367, filed Apr. 4, 2011, all of which is incorporated herein by reference in its entirety.

FIELD OF THE INVENTION

This invention is directed to the treatment of cancer, particularly uveal melanoma, with a dual inhibitor of MET and VEGF, such as a Compound of Formula I as disclosed herein.

BACKGROUND OF THE INVENTION

Uveal, or ocular, melanoma, which includes choroidal and iris melanomas, is the most common intraocular tumor found in adults. Tumors arise from the pigment cells, or melanocytes, that reside within the uvea that give color to the eye. Statistics indicate that up to 2000 individuals in the United States are diagnosed with ocular melanoma every year.

Once metastatic, ocular melanomas are highly fatal, and patients rarely live for more than a year after diagnosis. Although surgery and/or radiation therapy may be effective for treating ocular melanoma that is localized to the area around the eye, chemotherapy historically has been considered ineffective for treating metastasized ocular melanoma.

Abdel-Rahman and coworkers (Invest. Ophthalmol. Vis. Sci. 51, 7, 3333-3339 (2010)) recently observed a high frequency of overexpression of MET protein in ocular melanomas. MET plays important roles in cell motility, proliferation, and survival, and it has been shown to be a key factor in tumor angiogenesis, invasiveness, and metastasis. Prominent expression of MET has been observed in other tumor types. The high frequency of MET in ocular melanoma supports its role in the pathogenesis of these tumors and also suggests that MET is a potentially useful therapeutic target for treating ocular melanoma.

Thus, a need remains for methods of treating ocular melanoma, particularly by inhibiting MET.

SUMMARY OF THE INVENTION

These and other needs are met by the present invention, which is directed to a method for treating melanoma. The melanoma can be ocular melanoma, and more particularly choroidal melanoma or iris melanoma. The method comprises administering to a patient in need of such treatment a therapeutically effective amount of a compound that modulates MET.

In one aspect, the present invention is directed to a method for treating ocular melanoma comprising administering to a patient in need of such treatment a compound of

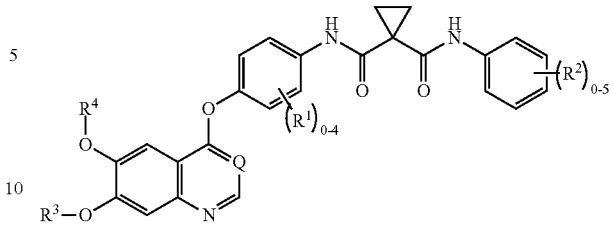

I or a pharmaceutically acceptable salt thereof, wherein:
$R^1$ is halo;
$R^2$ is halo;
$R^3$ is $(C_1-C_6)$alkyl;
$R^4$ is $(C_1-C_6)$alkyl; and
Q is CH or N.

In one embodiment, the compound of Formula I is a compound of Formula I(a)

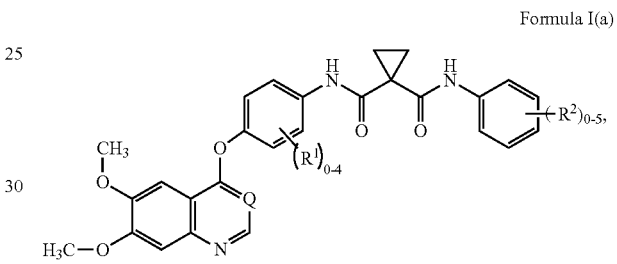

Formula I(a)

or a pharmaceutically acceptable salt thereof, wherein:
$R^1$ is halo;
$R^2$ is halo; and
Q is CH or N.

In another embodiment, the compound of Formula I is Compound 1:

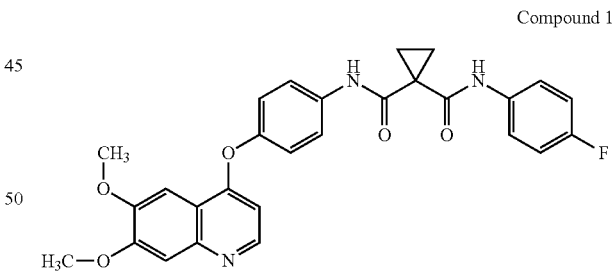

Compound 1 or a pharmaceutically acceptable salt thereof. Compound 1 is known as N-(4-{[6,7-bis(methyloxy)quinolin-4-yl]oxy}phenyl)-N'-(4-fluorophenyl)cyclopropane-1,1-dicarboxamide.

In another embodiment, the invention provides a method for treating metastatic ocular melanoma, comprising administering to a patient in need of such treatment a therapeutically effective amount of a pharmaceutical formulation comprising Compound of Formula I, Ia, or Compound 1 the malate salt of Compound of Formula I, Ia, or Compound 1, or another pharmaceutically acceptable salt of Compound of Formula I, Ia, or Compound 1.

Compound 1 is an orally bioavailable multitargeted tyrosine kinase inhibitor with potent activity against MET and VEGFR2. Compound 1 suppresses MET and VEGFR2 signaling, rapidly induces apoptosis of endothelial cells and tumor cells, and causes tumor regression in xenograft tumor models. Compound 1 also significantly reduces tumor invasiveness and metastasis and substantially improves overall survival in a murine pancreatic neuroendocrine tumor model. In a phase 1 clinical study, Compound 1 was generally well-tolerated, with fatigue, diarrhea, anorexia, rash, and palmar-plantar erythrodysesthesia being the most commonly observed adverse events.

BRIEF DESCRIPTION OF THE FIGURES

FIG. 2 summarizes the baseline mutation status of the ocular melanoma patients.

FIG. 3 summarizes the treatment status of the ocular melanoma patients.

FIGS. 4A and 4B provide an overview of the patients with the best response of SD or PR.

DETAILED DESCRIPTION OF THE INVENTION

Abbreviations and Definitions

Figure 1:
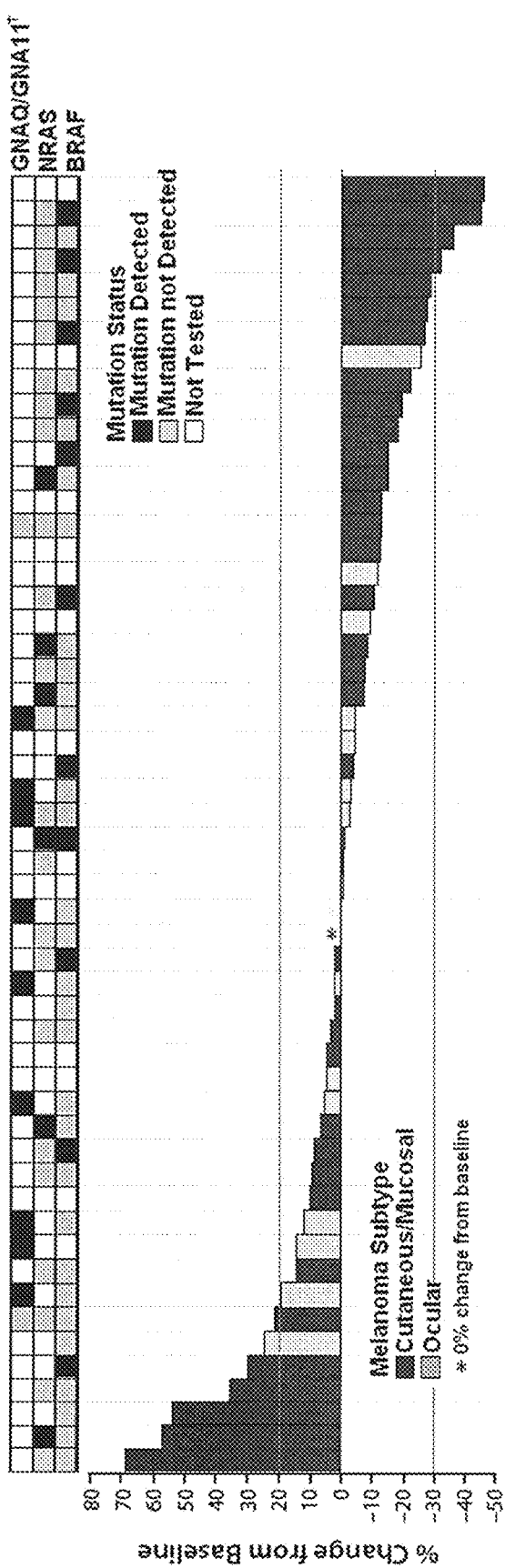
FIG. 1 summarizes the results of a Phase 2 study using Compound 1 in a cohort of patients with melanoma, including ocular melanoma.

The following abbreviations and terms have the indicated meanings throughout:

| Abbreviation | Meaning |
| --- | --- |
| Ac | Acetyl |
| Br | Broad |
| ° C. | degrees Celsius |
| c- | Cyclo |
| CBZ | CarboBenZoxy = benzyloxycarbonyl |
| d | Doublet |
| dd | doublet of doublet |
| dt | doublet of triplet |
| DCM | Dichloromethane |
| DME | 1,2-dimethoxyethane |
| DMF | N,N-dimethylformamide |
| DMSO | dimethyl sulfoxide |
| Dppf | 1,1'-bis(diphenylphosphano)ferrocene |
| EI | Electron Impact ionization |
| G | gram(s) |
| h or hr | hour(s) |
| HPLC | high pressure liquid chromatography |
| L | liter(s) |
| M | molar or molarity |
| m | Multiplet |
| Mg | milligram(s) |
| MHz | megahertz (frequency) |
| Min | minute(s) |
| mL | milliliter(s) |
| μL | microliter(s) |
| μM | Micromole(s) or micromolar |
| mM | Millimolar |
| Mmol | millimole(s) |
| Mol | mole(s) |
| MS | mass spectral analysis |
| N | normal or normality |
| nM | Nanomolar |
| NMR | nuclear magnetic resonance spectroscopy |
| q | Quartet |
| RT | Room temperature |
| s | Singlet |
| t or tr | Triplet |
| TFA | trifluoroacetic acid |
| THF | Tetrahydrofuran |
| TLC | thin layer chromatography |

The symbol "–" means a single bond, and "=" means a double bond.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

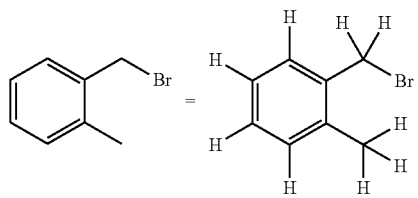

If a group "R" is depicted as "floating" on a ring system, as for example in the formula:

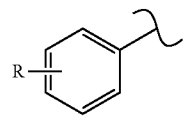

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

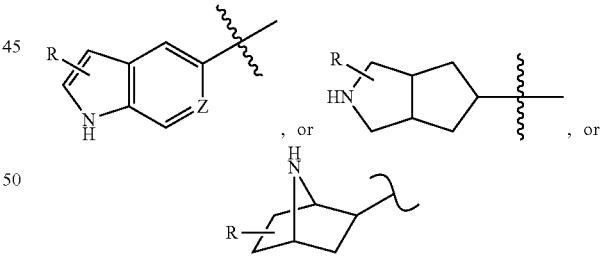

then, unless otherwise defined, a substituent "R" may reside on any atom of the fused ring system, assuming replacement of a depicted hydrogen (for example the —NH— in the formula above), implied hydrogen (for example, in the formula above, where the hydrogens are not shown but understood to be present), or expressly defined hydrogen (for example where in the formula above, "Z" equals =CH—) from one of the ring atoms, so long as a stable structure is formed. In the example depicted, the "R" group may reside on either the 5-membered or the 6-membered ring of the fused ring system.

When a group "R" is depicted as existing on a ring system containing saturated carbons, as for example in the formula:

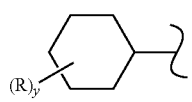

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

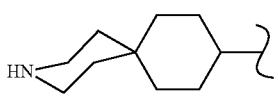

"Halogen" or "halo" refers to fluorine, chlorine, bromine, or iodine.

"Yield" for each of the reactions described herein is expressed as a percentage of the theoretical yield.

"Patient," for the purposes of the present invention, includes humans and other animals, particularly mammals, and other organisms. Thus the methods are applicable to both human therapy and veterinary applications. In one embodiment, the patient is a mammal, and in another embodiment, the patient is human.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17$^{th}$ ed., Mack Publishing Company, Easton, Pa., 1985, or S. M. Berge, et al., "Pharmaceutical Salts," J. Pharm. Sci., 1977; 66:1-19, both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, malic acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenyipropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid, and the like.

"Prodrug" refers to compounds that are transformed, (usually rapidly), in vivo to yield an active compound, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example, those between about one and about six carbons) the alkyl group is a straight or branched chain. Acceptable esters also include cycloalkyl esters and arylalkyl esters such as, but not limited to, benzyl. Examples of pharmaceutically acceptable amides of the compounds of this invention include, but are not limited to, primary amides and secondary and tertiary alkyl amides (for example, those between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series and Bioreversible Carriers in Drug Design, ed. Edward B. Roche, American Pharmaceutical Association and Pergamon Press, 1987, both of which are incorporated herein by reference for all purposes.

"Therapeutically effective amount" is an amount of a compound of the invention that, when administered to a patient, ameliorates a symptom of the disease. A therapeutically effective amount is intended to include an amount of a compound alone or in combination with other active ingredients. It will also be effective to modulate c-Met and/or VEGFR2 or to treat or prevent cancer. The amount of a compound of the invention which constitutes a "therapeutically effective amount" will vary depending on the compound, the disease state and its severity, the age of the patient to be treated, and other factors. The therapeutically effective amount can be determined by one of ordinary skill in the art.

"Treating" or "treatment" of a disease, disorder, or syndrome, as used herein, includes: (i) preventing the disease, disorder, or syndrome from occurring in a human, for instance, by causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, for instance, by arresting its development; and (iii) relieving the disease, disorder, or syndrome, for instance, by causing regression of the disease, disorder, or syndrome. As is known in the art, adjustments for systemic versus localized delivery, age, body weight, general health, sex, diet, time of administration, drug interaction, and the severity of the condition may be necessary, and will be ascertainable with routine experience.

All patents and patent publications cited herein that are assigned to the same assignee as the present invention are incorporated by reference in their entirety unless stated to the contrary.

Embodiments

In one embodiment the method employs a compound of Formula I:

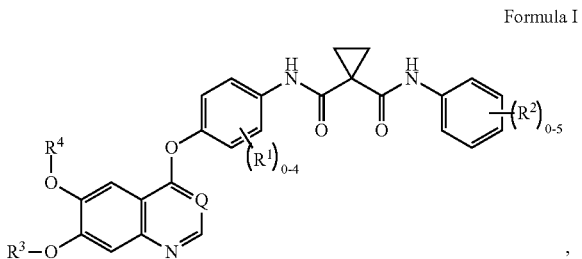

Formula I or a pharmaceutically acceptable salt thereof, wherein:
$R^1$ is halo;
$R^2$ is halo;
$R^3$ is $(C_1\text{-}C_6)$alkyl;
$R^4$ is $(C_1\text{-}C_6)$alkyl; and
Q is CH or N.

In another embodiment, the compound of Formula I is a compound of Formula I(a)

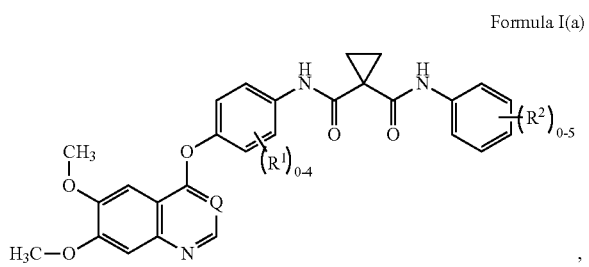

Formula I(a)

or a pharmaceutically acceptable salt thereof, wherein:
$R^1$ is halo;
$R^2$ is halo; and
Q is CH or N.

In another embodiment of the method, the compound of Formula I is Compound 1:

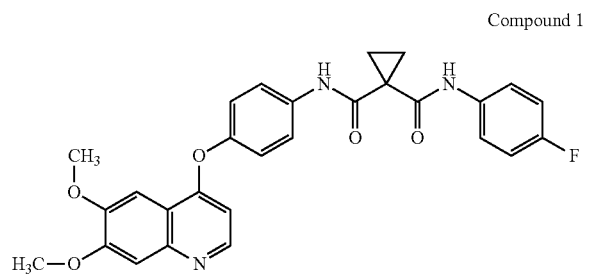 [SMILES: COc1cc2nccc(Oc3ccc(NC(=O)C4(C(=O)Nc5ccc(F)cc5)CC4)cc3)c2cc1OC]

Compound 1 or a pharmaceutically acceptable salt thereof. As indicated previously, Compound 1 is also known as N-(4-{[6,7-bis(methyloxy)quinolin-4-yl]oxy}phenyl)-N'-(4-fluorophenyl)cyclopropane-1,1-dicarboxamide. WO 2005/030140 describes the synthesis of N-(4-{[6,7-bis(methyloxy)quinolin-4-yl]oxy}phenyl)-N'-(4-fluorophenyl)cyclopropane-1,1-dicarboxamide (Example 12, 37, 38, and 48) and also discloses the therapeutic activity of this molecule to inhibit, regulate and/or modulate the signal transduction of kinases, (Assays, Table 4, entry 289). Example 48 is on paragraph [0353] in WO 2005/030140.

In other embodiments, the compound of Formula I, Ia, or Compound 1, or a pharmaceutically acceptable salt thereof, is administered as a pharmaceutical composition, wherein the pharmaceutical composition additionally comprises a pharmaceutically acceptable carrier, excipient, or diluent.

The compound of Formula I, Ia, and Compound 1, as described herein, includes both the recited compounds as well as individual isomers and mixtures of isomers. In each instance, the compound of Formula I, Ia, and Compound 1, includes the pharmaceutically acceptable salts, hydrates, and/or solvates of the recited compounds and any individual isomers or mixtures of isomers thereof.

In other embodiments, the compound of Formula I can be the (L)-malate salt. The malate salt of the Compound of Formula I, Ia, and of Compound 1 is disclosed in PCT/US2010/021194 and U.S. Ser. No. 61/325,095.

In other embodiments, the compound of Formula (I) can be the malate salt.

In other embodiments, the compound of Formula (I) can be the (D)-malate salt.

In other embodiments, the compound of Formula (I) can be the (L)-malate salt.

In other embodiments, the compound of Formula I(a) can be the malate salt.

In other embodiments, the compound of Formula I(a) can be the (D)-malate salt.

In other embodiments, the compound of Formula I(a) can be the (L)-malate salt.

In other embodiments, Compound 1 can be the malate salt.

In other embodiments, Compound 1 can be the (D)-malate salt.

In other embodiments, the compound of Formula (I) can be the (L)-malate salt of Compound 1.

In another embodiment, the malate salt is in the crystalline N-1 form of the (L) malate salt and/or the (D) malate salt of Compound 1 as disclosed in PCT/US10/021194, which is incorporated herein by reference in its entirety.

In another embodiment, the invention is directed to a method for ameliorating the symptoms of ocular melanoma, comprising administering to a patient in need of such treatment a therapeutically effective amount of a compound of Formula I in any of the embodiments disclosed herein.

Administration

Administration of the compound of Formula I, Ia, or Compound 1, or a pharmaceutically acceptable salt thereof, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally; in the form of solid, semi-solid, lyophilized powder, or liquid dosage forms, such as, for example, tablets, suppositories, pills, soft elastic and hard gelatin dosages (which can be in capsules or tablets), powders, solutions, suspensions, or aerosols, or the like, specifically in unit dosage forms suitable for simple administration of precise dosages.

The compositions will include a conventional pharmaceutical carrier or excipient and a compound of Formula I as the/an active agent and, in addition, may include carriers, adjuvants, and the like.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the compound of Formula I may also contain minor amounts of auxiliary substances such as wetting or emulsifying agents, pH buffering agents, and antioxidants, such as citric acid, sorbitan monolaurate, triethanolamine oleate, butylalted hydroxytoluene, etc.

The choice of formulation depends on various factors such as the mode of drug administration (e.g., for oral administration, formulations in the form of tablets, pills, or capsules) and the bioavailability of the drug substance. Recently, pharmaceutical formulations have been developed, especially for drugs that show poor bioavailability based upon the principle that bioavailability can be increased by increasing the surface area, for instance, by decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include: water, ethanol, polyols (propyleneglycol, polyethyleneglycol, glycerol, and the like), suitable mixtures thereof, vegetable oils (such as olive oil), and injectable organic esters (such as ethyl oleate). Proper fluidity can be maintained, for example, by the use of a coating such as lecithin, by the maintenance of the required particle size in the case of dispersions, and by the use of surfactants.

One specific route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, for example, cellulose derivatives, starch, alignates, gelatin, polyvinylpyrrolidone, sucrose, and gum acacia, (c) humectants, for example, glycerol, (d) disintegrating agents, for example, agar-agar, calcium carbonate, potato or tapioca starch, alginic acid, croscarmellose sodium, complex silicates, and sodium carbonate, (e) solution retarders, for example paraffin, (f) absorption accelerators, as for example, quaternary ammonium compounds, (g) wetting agents, for example, cetyl alcohol, and glycerol monostearate, magnesium stearate, and the like (h) adsorbents, for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms, as described above, can be prepared with coatings and shells, such as enteric coatings and others well known in the art. They may contain pacifying agents and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the compound of Formula I, or a pharmaceutically acceptable salt thereof, and optional pharmaceutical adjuvants in a carrier, such as water, saline, aqueous dextrose, glycerol, ethanol, and the like; solubilizing agents and emulsifiers, such as, ethyl alcohol, isopropyl alcohol, ethyl carbonate, ethyl acetate, benzyl alcohol, benzyl benzoate, propyleneglycol, 1,3-butyleneglycol, or dimethylformamide; oils, in particular, cottonseed oil, groundnut oil, corn germ oil, olive oil, castor oil, and sesame oil; glycerol, tetrahydrofurfuryl alcohol, polyethyleneglycols, and fatty acid esters of sorbitan; or mixtures of these substances and the like, to thereby form a solution or suspension.

Suspensions, in addition to the active compounds, may contain suspending agents, for example, ethoxylated isostearyl alcohols, polyoxyethylene sorbitol, and sorbitan esters, microcrystalline cellulose, aluminum metahydroxide, bentonite, agar-agar, and tragacanth, mixtures of these substances, and the like.

Compositions for rectal administration are, for example, suppositories that can be prepared by mixing the compound of Formula I with, for example, suitable non-irritating excipients or carriers such as cocoa butter, polyethyleneglycol, or a suppository wax, which are solid at ordinary temperatures but liquid at body temperature and therefore melt while in a suitable body cavity, releasing the active component therein.

Dosage forms for topical administration of the compound of Formula I include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this disclosure.

Compressed gases may be used to disperse the compound of Formula I in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of Formula I, or a pharmaceutically acceptable salt thereof, and 99% to 1% by weight of a suitable pharmaceutical excipient. In one example, the composition will be between about 5% and about 75% by weight of a compound(s) of Formula I, Ia, or Compound 1, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in all cases, contain a therapeutically effective amount of a compound of Formula I, or a pharmaceutically acceptable salt thereof, for treatment of a disease-state in accordance with the teachings of this disclosure.

The compounds of this disclosure, or their pharmaceutically acceptable salts or solvates, are administered in a therapeutically effective amount which will vary depending upon a variety of factors including: the activity of the specific compound employed, the metabolic stability and length of action of the compound, the age, body weight, general health, sex, diet, mode and time of administration, rate of excretion, drug combination, the severity of the particular disease-states, and the host undergoing therapy. The compound of Formula I, Ia, or Compound 1, can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors, including the requirements of the patient, the severity of the condition being treated, and the pharmacological activity of the compound being used. The determination of optimum dosages for a particular patient is well known to one of ordinary skill in the art.

In other embodiments, the compound of Formula I, Ia, or Compound 1 can be administered to the patient concurrently with other cancer treatments. Such treatments include other cancer chemotherapeutics, hormone replacement therapy, radiation therapy, or immunotherapy, among others. The choice of other therapy will depend on a number of factors including the metabolic stability and length of action of the compound, the age, body weight, general health, sex, diet, mode and time of administration, rate of excretion, drug combination, the severity of the particular disease-states, and the host undergoing therapy.

Preparation of the Compound 1

Preparation of N-(4-{[6,7-bis(methyloxy)quinolin-4-yl]oxy}phenyl)-N'-(4-fluorophenyl)cyclopropane-1,1-dicarboxamide and the (L)-malate salt thereof.

The synthetic route used for the preparation of N-(4-{[6,7-bis(methyloxy)quinolin-4-yl]oxy}phenyl)-N'-(4-fluorophenyl)cyclopropane-1,1-dicarboxamide and the (L)-malate salt thereof is depicted in Scheme 1.

Scheme 1

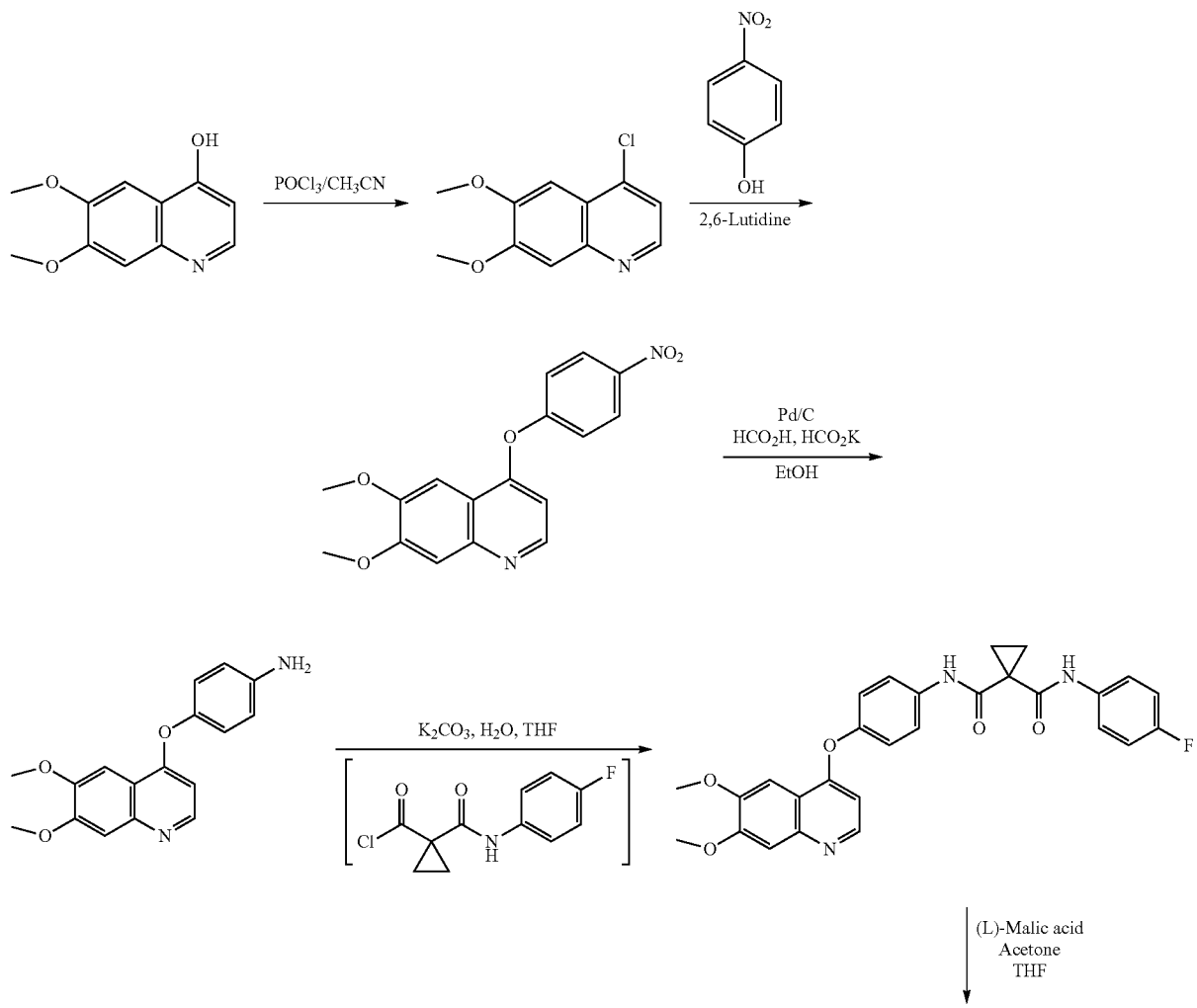

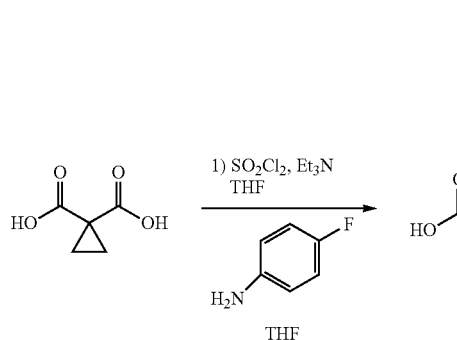
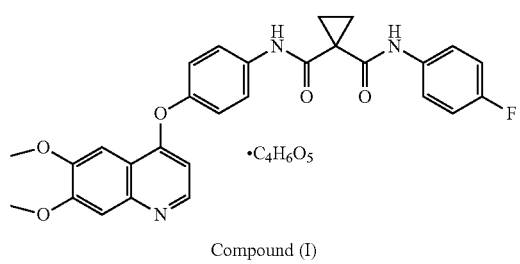

Compound (I)

Preparation of 4-Chloro-6,7-dimethoxy-quinoline

A reactor was charged sequentially with 6,7-dimethoxy-quinoline-4-ol (10.0 kg) and acetonitrile (64.0 L). The resulting mixture was heated to approximately 65° C. and phosphorus oxychloride (POCl₃, 50.0 kg) was added. After the addition of POCl₃, the temperature of the reaction mixture was raised to approximately 80° C. The reaction was deemed complete (approximately 9.0 hours) when less than 2 percent of the starting material remained (in process high-performance liquid chromotography [HPLC] analysis). The reaction mixture was cooled to approximately 10° C. and then quenched into a chilled solution of dichloromethane (DCM, 238.0 kg), 30 percent NH₄OH (135.0 kg), and ice (440.0 kg). The resulting mixture was warmed to approximately 14° C., and phases were separated. The organic phase was washed with water (40.0 kg) and concentrated by vacuum distillation with the removal of solvent (approximately 190.0 kg). Methyl-t-butyl ether (MTBE, 50.0 kg) was added to the batch, and the mixture was cooled to approximately 10° C., during which time the product crystallized out. The solids were recovered by centrifugation, washed with n heptane (20.0 kg), and dried at approximately 40° C. to afford the title compound (8.0 kg).

Preparation of 6,7-Dimethyl-4-(4-nitro-phenoxy)-quinoline

A reactor was sequentially charged with 4-chloro-6,7-dimethoxy-quinoline (8.0 kg), 4 nitrophenol (7.0 kg), 4 dimethylaminopyridine (0.9 kg), and 2,6-lutidine (40.0 kg). The reactor contents were heated to approximately 147° C. When the reaction was complete (less than 5% starting material remaining as determined by in process HPLC analysis, approximately 20 hours), the reactor contents were allowed to cool to approximately 25° C. Methanol (26.0 kg) was added, followed by potassium carbonate (3.0 kg) dissolved in water (50.0 kg). The reactor contents were stirred for approximately 2 hours. The resulting solid precipitate was filtered, washed with water (67.0 kg), and dried at 25° C. for approximately 12 hours to afford the title compound (4.0 kg).

Preparation of 4-(6,7-Dimethoxy-quinoline-4-yloxy)-phenylamine

A solution containing potassium formate (5.0 kg), formic acid (3.0 kg), and water (16.0 kg) was added to a mixture of 6,7-dimethoxy-4-(4-nitro-phenoxy)-quinoline (4.0 kg), 10% palladium on carbon (50 percent water wet, 0.4 kg) in tetrahydrofuran (40.0 kg) that had been heated to approximately 60° C. The addition was carried out such that the temperature of the reaction mixture remained approximately 60° C. When the reaction was deemed complete as determined using in-process HPLC analysis (less than 2 percent starting material remaining, typically 1.5-15 hours), the reactor contents were filtered. The filtrate was concentrated by vacuum distillation at approximately 35° C. to half of its original volume, which resulted in the precipitation of the product. The product was recovered by filtration, washed with water (12.0 kg), and dried under vacuum at approximately 50° C. to afford the title compound (3.0 kg; 97 percent AUC).

Preparation of 1-(4-Fluoro-phenylcarbamoyl)-cyclopropanecarboxylic Acid

Triethylamine (8.0 kg) was added to a cooled (approximately 4° C.) solution of commercially available cyclopropane-1,1-dicarboxylic acid (10.0 kg) in THF (63.0 kg) at a rate such that the batch temperature did not exceed 10° C. The solution was stirred for approximately 30 minutes, and then thionyl chloride (9.0 kg) was added, keeping the batch temperature below 10° C. When the addition was complete, a solution of 4-fluoroaniline (9.0 kg) in THF (25.0 kg) was added at a rate such that the batch temperature did not exceed 10° C. The mixture was stirred for approximately 4 hours and then diluted with isopropyl acetate (87.0 kg). This solution was washed sequentially with aqueous sodium hydroxide (2.0 kg dissolved in 50.0 L of water), water (40.0 L), and aqueous sodium chloride (10.0 kg dissolved in 40.0 L of water). The organic solution was concentrated by vacuum distillation followed by the addition of heptane, which resulted in the precipitation of solid. The solid was recovered by centrifugation and then dried at approximately 35° C. under vacuum to afford the title compound (10.0 kg).

Preparation of 1-(4-Fluoro-phenylcarbamoyl)-cyclopropanecarbonyl Chloride

Oxalyl chloride (1.0 kg) was added to a solution of 1-(4-fluoro-phenylcarbamoyl)-cyclopropanecarboxylic acid (2.0 kg) in a mixture of THF (11 kg) and N, N-dimethylformamide (DMF; 0.02 kg) at a rate such that the batch temperature did not exceed 30° C. This solution was used in the next step without further processing.

Preparation of N-(4-{[6,7-bis(methyloxy)quinolin-4-yl]oxy}phenyl)-N'-(4-fluorophenyl)cyclopropane-1,1-dicarboxamide The solution from the previous step containing 1-(4-fluoro-phenylcarbamoyl)-cyclopropanecarbonyl chloride was added to a mixture of 4-(6,7-dimethoxy-quinoline-4-yloxy)-phenylamine (3.0 kg), and potassium carbonate (4.0 kg) in THF (27.0 kg), and water (13.0 kg) at a rate such that the batch temperature did not exceed 30° C. When the reaction was complete (approximately 10 minutes), water (74.0 kg) was added. The mixture was stirred at 15 to 30° C. for approximately 10 hours, which resulted in the precipitation of the product. The product was recovered by filtration, washed with a pre made solution of THF (11.0 kg) and water (24.0 kg), and dried at approximately 65° C. under vacuum for approximately 12 hours to afford the title compound (free base, 5.0 kg). $^1$H NMR (400 MHz, $d_6$-DMSO): δ 10.2 (s, 1H), 10.05 (s, 1H), 8.4 (s, 1H), 7.8 (m, 2H), 7.65 (m, 2H), 7.5 (s, 1H), 7.35 (s, 1H), 7.25 (m, 2H), 7.15 (m, 2H), 6.4 (s, 1H), 4.0 (d, 6H), 1.5 (s, 4H). LC/MS: M+H=502.

Preparation of N-(4-{[6,7-bis(methyloxy)quinolin-4-yl]oxy}phenyl)-N'-(4-fluorophenyl)cyclopropane-1,1-dicarboxamide, (L) Malate Salt A solution of L-malic acid (2.0 kg) in water (2.0 kg) was added to a solution of Cyclopropane-1,1-dicarboxylic acid [4-(6,7-dimethoxy-quinoline-4-yloxy)-phenyl]-amide (4-fluoro-phenyl)-amide free base (15, 5.0 kg) in ethanol, maintaining a batch temperature of approximately 25° C. Carbon (0.5 kg) and thiol silica (0.1 kg) were then added, and the resulting mixture was heated to approximately 78° C., at which point water (6.0 kg) was added. The reaction mixture was then filtered, followed by the addition of isopropanol (38.0 kg). The reaction mixture was allowed to cool to approximately 25° C. The product was recovered by filtration and washed with isopropanol (20.0 kg) and dried at approximately 65° C. to afford the title compound (5.0 kg).

An alternative route that for the preparation of Compound 1 is depicted in Scheme 2.

Scheme 2
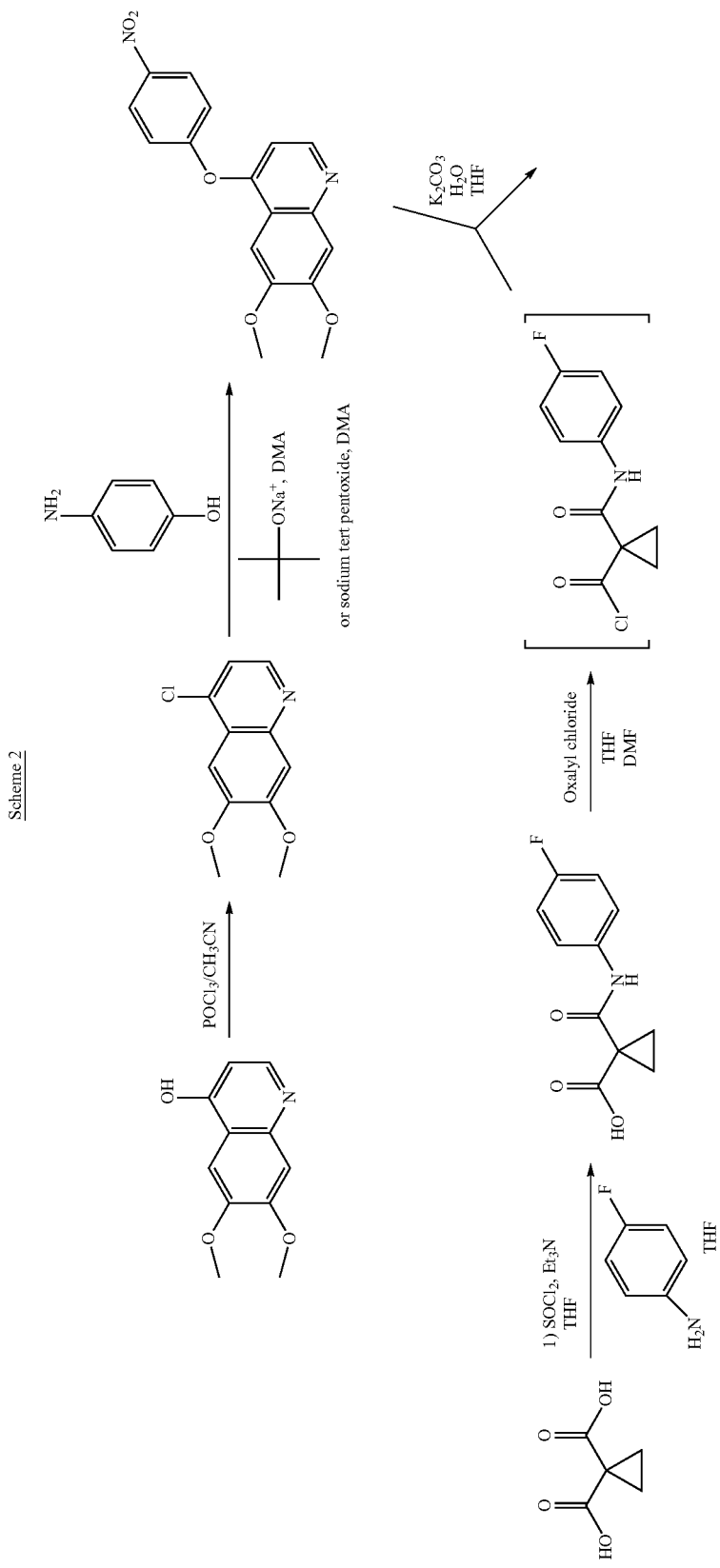

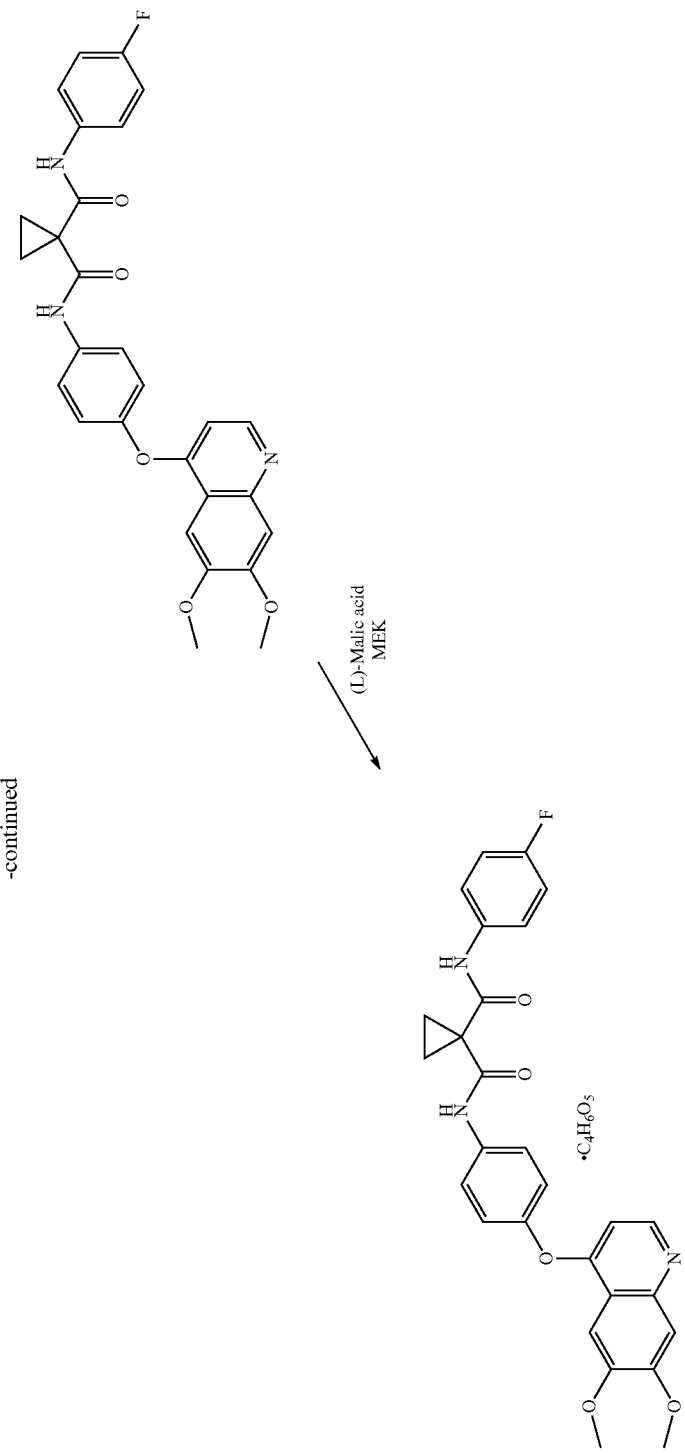

Preparation of 4-Chloro-6,7-dimethoxy-quinoline

A reactor was charged sequentially with 6,7-dimethoxy-quinoline-4-ol (47.0 kg) and acetonitrile (318.8 kg). The resulting mixture was heated to approximately 60° C. and phosphorus oxychloride (POCl$_3$, 130.6 kg) was added. After the addition of POCl$_3$, the temperature of the reaction mixture was raised to approximately 77° C. The reaction was deemed complete (approximately 13 hours) when less than 3 percent of the starting material remained (in-process high-performance liquid chromatography [HPLC] analysis). The reaction mixture was cooled to approximately 2 to 7° C. and then quenched into a chilled solution of dichloromethane (DCM, 482.8 kg), 26 percent NH$_4$OH (251.3 kg), and water (900 L). The resulting mixture was warmed to approximately 20 to 25° C., and phases were separated. The organic phase was filtered through a bed of AW hyflo super-cel NF (Celite; 5.4 kg), and the filter bed was washed with DCM (118.9 kg). The combined organic phase was washed with brine (282.9 kg) and mixed with water (120 L). The phases were separated and the organic phase was concentrated by vacuum distillation with the removal of solvent (approximately 95 L residual volume). DCM (686.5 kg) was charged to the reactor containing organic phase and concentrated by vacuum distillation with the removal of solvent (approximately 90 L residual volume). Methyl t-butyl ether (MTBE, 226.0 kg) was then charged and the temperature of the mixture was adjusted to −20 to 25° C. and held for 2.5 hours. This resulted in solid precipitate, which was then filtered, washed with n-heptane (92.0 kg), and dried on a filter at approximately 25° C. under nitrogen to afford the title compound. (35.6 kg).

Preparation of 4-(6,7-Dimethoxy-quinoline-4-yloxy)-phenylamine

4-Aminophenol (24.4 kg) dissolved in N,N-dimethylacetamide (DMA, 184.3 kg) was charged to a reactor containing 4-chloro-6,7-dimethoxyquinoline (35.3 kg), sodium t-butoxide, (21.4 kg) and DMA (167.2 kg) at 20 to 25° C. This mixture was then heated to 100 to 105° C. for approximately 13 hours. After the reaction was deemed complete as determined using in-process HPLC analysis (less than 2 percent starting material remaining), the reactor contents were cooled at 15 to 20° C. and water (pre-cooled, 2 to 7° C., 587 L) charged at a rate to maintain 15 to 30° C. temperature. The resulting solid precipitate was filtered, washed with a mixture of water (47 L) and DMA (89.1 kg) and finally with water (214 L). The filter cake was then dried at approximately 25° C. on filter to yield crude 4-(6,7-dimethoxy-quinoline-4-yloxy)-phenylamine (59.4 kg wet, 41.6 kg dry calculated based on LOD). Crude 4-(6,7-dimethoxy-quinoline-4-yloxy)-phenylamine was refluxed (approximately 75° C.) in a mixture of tetrahydrofuran (THF, 211.4 kg) and DMA (108.8 kg) for approximately 1 hour and then cooled to 0 to 5° C. and aged for approximately 1 hour after which time the solid was filtered, washed with THF (147.6 kg), and dried on a filter under vacuum at approximately 25° C. to yield 4-(6,7-dimethoxy-quinoline-4-yloxy)-phenylamine (34.0 kg).

Alternative Preparation of 4-(6,7-Dimethoxy-quinoline-4-yloxy)-phenylamine 4-chloro-6,7-dimethoxyquinoline (34.8 kg) and 4-Aminophenol (30.8 kg) and sodium tert pentoxide (1.8 equivalents) 88.7 kg, 35 wt percent in THF) were charged to a reactor, followed by N,N-dimethylacetamide (DMA, 293.3 kg). This mixture was then heated to 105 to 115° C. for approximately 9 hours. After the reaction was deemed complete as determined using in-process HPLC analysis (less than 2 percent starting material remaining), the reactor contents were cooled at 15 to 25° C., and water (315 kg) was added over a two hour period while maintaining the temperature between 20 and 30° C. The reaction mixture was then agitated for an additional hour at 20 to 25° C. The crude product was collected by filtration and washed with a mixture of water (88 kg) and DMA (82.1 kg), followed by water (175 kg). The product was dried on a filter drier for 53 hours. The LOD showed less than 1 percent weight/weight (w/w).

In an alternative procedure, 1.6 equivalents of sodium tert-pentoxide were used, and the reaction temperature was increased from 110 to 120° C. In addition, the cool down temperature was increased to 35 to 40° C., and the starting temperature of the water addition was adjusted to 35 to 40° C., with an allowed exotherm to 45° C.

Preparation of 1-(4-Fluoro-phenylcarbamoyl)-cyclopropanecarboxylic Acid

Triethylamine (19.5 kg) was added to a cooled (approximately 5° C.) solution of cyclopropane-1,1-dicarboxylic acid (24.7 kg) in THF (89.6 kg) at a rate such that the batch temperature did not exceed 5° C. The solution was stirred for approximately 1.3 hours, and then thionyl chloride (23.1 kg) was added, keeping the batch temperature below 10° C. When the addition was complete, the solution was stirred for approximately 4 hours keeping the temperature below 10° C. A solution of 4-fluoroaniline (18.0 kg) in THF (33.1 kg) was then added at a rate such that the batch temperature did not exceed 10° C. The mixture was stirred for approximately 10 hours, after which the reaction was deemed complete. The reaction mixture was then diluted with isopropyl acetate (218.1 kg). This solution was washed sequentially with aqueous sodium hydroxide (10.4 kg, 50% dissolved in 119 L of water), further diluted with water (415 L), then with water (100 L), and finally with aqueous sodium chloride (20.0 kg dissolved in 100 L of water). The organic solution was concentrated by vacuum distillation (100 L residual volume) below 40° C., followed by the addition of n-heptane (171.4 kg), which resulted in the precipitation of solid. The solid was recovered by filtration and washed with n-Heptane (102.4 kg), resulting in wet crude, 1-(4-fluoro-phenylcarbamoyl)-cyclopropanecarboxylic acid (29.0 kg). The crude, 1-(4-fluoro-phenylcarbamoyl)-cyclopropanecarboxylic acid was dissolved in methanol (139.7 kg) at approximately 25° C., followed by the addition of water (320 L), resulting in slurry which was recovered by filtration, washed sequentially with water (20 L) and n-heptane (103.1 kg), and then dried on the filter at approximately 25° C. under nitrogen to afford the title compound (25.4 kg).

Preparation of 1-(4-Fluoro-phenylcarbamoyl)-cyclopropanecarbonyl Chloride

Oxalyl chloride (12.6 kg) was added to a solution of 1-(4-fluoro-phenylcarbamoyl)-cyclopropanecarboxylic acid (22.8 kg) in a mixture of THF (96.1 kg) and N, N-dimethylformamide (DMF; 0.23 kg) at a rate such that the batch temperature did not exceed 25° C. This solution was used in the next step without further processing.

Alternative Preparation of 1-(4-Fluoro-phenylcarbamoyl)-cyclopropanecarbonyl Chloride A reactor was charged with 1-(4-fluoro-phenylcarbamoyl)-cyclopropanecarboxylic acid (35 kg), DMF (344 g), and THF (175 kg). The reaction mixture was adjusted to 12 to 17° C., and then to the reaction mixture was charged 19.9 kg of oxalyl chloride over a period of 1 hour. The reaction mixture was left stirring at 12 to 17° C. for 3 to 8 hours. This solution was used in the next step without further processing.

Preparation of Cyclopropane-1,1-dicarboxylic acid [4-(6,7-dimethoxy-quinoline-4-yloxy)-phenyl]-amide (4-fluoro-phenyl)-amide The solution from the previous step containing 1-(4-fluoro-phenylcarbamoyl)-cyclopropanecarbonyl chloride was added to a mixture of compound 4-(6,7-dimethoxy-quinoline-4-yloxy)-phenylamine (23.5 kg) and potassium carbonate (31.9 kg) in THF (245.7 kg) and water (116 L) at a rate such that the batch temperature did not exceed 30° C. When the reaction was complete (in approximately 20 minutes), water (653 L) was added. The mixture was stirred at 20 to 25° C. for approximately 10 hours, which resulted in the precipitation of the product. The product was recovered by filtration, washed with a pre-made solution of THF (68.6 kg) and water (256 L), and dried first on a filter under nitrogen at approximately 25° C. and then dried at approximately 45° C. under vacuum to afford the title compound (41.0 kg, 38.1 kg, calculated based on LOD).

Alternative Preparation of Cyclopropane-1,1-dicarboxylic Acid [4-(6,7-dimethoxy-quinolone-4-yloxy)-phenyl]-amide (4-fluoro-phenyl)-amide A reactor was charged with 4-(6,7-dimethoxy-quinoline-4-yloxy)-phenylamine (35.7 kg, 1 equivalent), followed by THF (412.9 kg). To the reaction mixture was charged a solution of K$_2$CO$_3$ (48.3 g) in water (169 kg). The acid chloride solution described in the Alternative preparation of 1-(4-Fluoro-phenylcarbamoyl)-cyclopropanecarbonyl chloride above was transferred to the reactor containing 4-(6,7-dimethoxy-quinoline-4-yloxy)-phenylamine while maintaining the temperature between 20 to 30° C. over a minimum of two hours. The reaction mixture was stirred at 20 to 25° C. for a minimum of three hours. The reaction temperature was then adjusted to 30 to 25° C., and the mixture was agitated. The agitation was stopped and the phases of the mixture were allowed to separate. The lower aqueous phase was removed and discarded. Water (804 kg) was added to the remaining upper organic phase. The reaction was left stirring at 15 to 25° C. for a minimum of 16 hours.

The product precipitated. The product was filtered and washed with a mixture of water (179 kg) and THF (157.9 kg) in two portions. The crude product was dried under a vacuum for at least two hours. The dried product was then taken up in THF (285.1 kg). The resulting suspension was transferred to reaction vessel and agitated until the suspension became a clear (dissolved) solution, which required heating to 30 to 35° C. for approximately 30 minutes. Water (456 kg) was then added to the solution, as well as SDAG-1 (20 kg) ethanol (ethanol denatured with methanol over two hours). The mixture was agitated at 15-25° C. for at least 16 hours. The product was filtered and washed with a mixture of water (143 kg) and THF (126.7 kg) in two portions. The product was dried at a maximum temperature set point of 40° C.

In an alternative procedure, the reaction temperature during acid chloride formation was adjusted to 10 to 15° C. The recrystallization temperature was changed from 15 to 25° C. to 45 to 50° C. for 1 hour and then cooled to 15 to 25° C. over 2 hours.

Preparation of Cyclopropane-1,1-dicarboxylic acid [4-(6,7-dimethoxy-quinoline-4-yloxy)-phenyl]-amide (4-fluoro-phenyl)-amide, (L) Malate Salt Cyclopropane-1,1-dicarboxylic acid [4-(6,7-dimethoxy-quinoline-4-yloxy)-phenyl]-amide (4-fluoro-phenyl)-amide (13.3 kg), L-malic acid (4.96 kg), methyl ethyl ketone (MEK; 188.6 kg), and water (37.3 kg) were charged to a reactor, and the mixture was heated to reflux (approximately 74° C.) for approximately 2 hours. The reactor temperature was reduced to 50 to 55° C., and the reactor contents were filtered. These sequential steps described above were repeated two more times starting with similar amounts of cyclopropane-1,1-dicarboxylic acid [4-(6,7-dimethoxy-quinoline-4-yloxy)-phenyl]-amide (4-fluoro-phenyl)-amide (13.3 kg), L-Malic acid (4.96 kg), MEK (198.6 kg), and water (37.2 kg). The combined filtrate was azeotropically dried at atmospheric pressure using MEK (1133.2 kg) (approximate residual volume 711 L; KF≤0.5% w/w) at approximately 74° C. The temperature of the reactor contents was reduced to 20 to 25° C. and held for approximately 4 hours, resulting in solid precipitate which was filtered, washed with MEK (448 kg), and dried under vacuum at 50° C. to afford the title compound (45.5 kg).

Alternative Preparation of Cyclopropane-1,1-dicarboxylic acid [4-(6,7-dimethoxy-quinoline-4-yloxy)-phenyl]-amide (4-fluoro-phenyl)-amide, (L) Malate Salt Cyclopropane-1,1-dicarboxylic acid [4-(6,7-dimethoxy-quinoline-4-yloxy)-phenyl]-amide (4-fluoro-phenyl)-amide (47.9 kg), L-malic acid (17.2), 658.2 kg methyl ethyl ketone, and 129.1 kg water (37.3 kg) were charged to a reactor, and the mixture was heated 50 to 55° C. for approximately 1 to 3 hours, and then at 55 to 60° C. for an additional 4 to 5 hours. The mixture was clarified by filtration through a 1 μm cartridge. The reactor temperature was adjusted to 20 to 25° C. and vacuum distilled with a vacuum at 150-200 mm Hg with a maximum jacket temperature of 55° C. to the volume range of 558-731 L.

The vacuum distillation was performed two more times with the charge of 380 kg and 380.2 kg methyl ethyl ketone, respectively. After the third distillation, the volume of the batch was adjusted to 18 volume/weight (v/w) of cyclopropane-,1-dicarboxylic acid [4-(6,7-dimethoxy-quinoline-4-yloxy)-phenyl]amide (4-fluoro-phenyl)-amide by charging methyl ethyl ketone (159.9 kg) to give a total volume of 880 L. An addition al vacuum distillation was carried out by adjusting methyl ethyl ketone (245.7 kg). The reaction mixture was left with moderate agitation at 20 to 25° C. for at least 24 hours. The product was filtered and washed with methyl ethyl ketone (415.1 kg) in three portions. The product was dried under a vacuum with the jacket temperature set point at 45° C.

In an alternative procedure, the order of addition was changes so that a solution of L-malic acid (17.7 kg) dissolved in water (129.9 kg) was added to cyclopropane-1,1- dicarboxylic acid [4-(6,7-dimethoxy-quinoline-4-yloxy)-phenyl]-amide (4-fluoro-phenyl)-amide (48.7 kg) in methyl ethyl ketone (673.3 kg).

Clinical Results

Compound 1 was used in a Phase 2 randomized discontinuation trial study of adults with melanoma, including ocular melanoma (See NCT00940225, Abstract 371). Compound 1 was administered at a daily dose of 100 mg (125 mg salt equivalent). The study endpoints included objective response rate (ORR) per mRECIST in the lead-in stage, and progression-free survival in the randomized stage.

The eligibility criteria included: (a) pathologically and radiologically confirmed diagnosis of advanced melanoma; (b) cutaneous, mucosal, or ocular subtypes; (c) up to two lines of prior systemic treatment (not including immunotherapy); (d) documented progressive disease and measurable target lesion(s) per mRECIST; and (e) no known brain metastases. Tumors were assessed by CT/MRI at baseline and every 6 weeks thereafter. Archival tumor tissue was retained for genotyping and biomarker analysis.

Objective tumor shrinkage was observed in sixty percent of the patients with melanoma who were enrolled in the study.

In all, 18 patients (28 percent) with ocular melanoma were enrolled. The results are summarized in FIG. 1-4. FIGS. 1 through 4 show a positive response to treatment with Compound 1 in patients of ocular melanoma. FIG. 1 presents mutation data based on archival tumor tissue and investigator reporting. Analyses for ocular melanoma were typically limited to commonly mutated GNAQ and GNA1, as well as BRAF. One partial response was observed at week 6.

FIG. 2 summarizes the baseline mutation status for patients in the study. Analyses for ocular melanoma were typically limited to commonly mutated GNAQ and GNA1, as well as BRAF. Analyses for non-ocular subtypes were generally limited to BRAF, NRAS, and KIT.

FIG. 3 summarizes the results. Eight of the fourteen patients with ocular melanoma who were tested showed a positive disease control rate.

FIGS. 4A and 4B provide an overview of patients with the best response rate. Patients with ocular melanoma (Patients 5, 6, 14, 15, 18, 20, 22, 26, 28, and 29) all showed stable disease.

At week 12, Compound 1 showed a positive disease control rate of 14 percent in patients with ocular cancer. At six months, Compound 1 showed evidence of objective tumor regression in 48 percent of the patients with ocular cancer.

Other Embodiments

The foregoing disclosure has been described in some detail by way of illustration and example, for purposes of clarity and understanding. The invention has been described with reference to various specific and preferred embodiments and techniques. It should be understood, however, that many variations and modifications can be made while remaining within the spirit and scope of the invention. It will be obvious to one of skill in the art that changes and modifications can be practiced within the scope of the appended claims. It is to be understood that the above description is intended to be illustrative and not restrictive.

The scope of the invention should, therefore, be determined not with reference to the above description, but should instead be determined with reference to the following appended claims, along with the full scope of equivalents to which such claims are entitled.

The invention claimed is:

1. A method for treating metastatic ocular melanoma, comprising administering to a patient in need of such treatment a therapeutically effective amount of Compound 1:

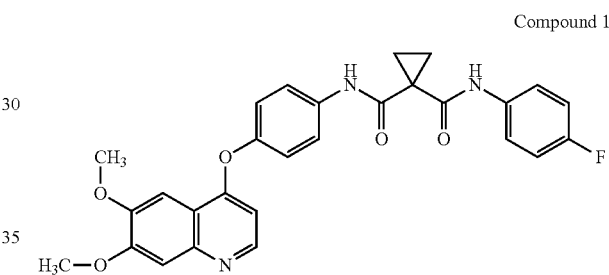

Compound 1 or a pharmaceutically acceptable salt thereof.

2. The method of claim 1, wherein the ocular melanoma is choroidal or iris melanoma.

3. The method of claim 1, wherein Compound 1 is the (L)- or (D)-malate salt.

4. The method of claim 3, wherein Compound 1 or a pharmaceutically acceptable salt thereof, is administered as a pharmaceutical composition comprising a pharmaceutically acceptable carrier, excipient, or diluent.

* * * * *